United States Patent
Melsheimer

(10) Patent No.: US 9,414,879 B2
(45) Date of Patent: Aug. 16, 2016

(54) CATALYZED EXOTHERMIC ABLATION DEVICE

(71) Applicant: Cook Medical Technologies LLC, Bloomington, IN (US)

(72) Inventor: Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 121 days.

(21) Appl. No.: 14/202,956

(22) Filed: Mar. 10, 2014

(65) Prior Publication Data

US 2014/0276716 A1    Sep. 18, 2014

Related U.S. Application Data

(60) Provisional application No. 61/777,051, filed on Mar. 12, 2013.

(51) Int. Cl.
*A61B 18/06* (2006.01)
*A61B 18/00* (2006.01)

(52) U.S. Cl.
CPC ........... *A61B 18/06* (2013.01); *A61B 2018/005* (2013.01); *A61B 2018/00333* (2013.01); *A61B 2018/00446* (2013.01); *A61B 2018/00494* (2013.01); *A61B 2018/00529* (2013.01); *A61B 2018/00535* (2013.01); *A61B 2018/00541* (2013.01); *A61B 2018/00565* (2013.01); *A61B 2018/00577* (2013.01); *A61B 2018/066* (2013.01)

(58) Field of Classification Search
CPC ............. A61B 2018/0041; A61B 2018/00166; A61B 2018/00011; A61B 2018/068; A61B 2018/062; A61B 2018/066; A61F 2007/025; A61F 2007/0293; A61F 7/03
See application file for complete search history.

(56) References Cited

U.S. PATENT DOCUMENTS

| | | | |
|---|---|---|---|
| 3,212,255 A | 10/1965 | Putt et al. | |
| 4,292,208 A | 9/1981 | Baldi et al. | |
| 4,796,622 A * | 1/1989 | Lu | A61B 17/22 606/28 |
| 4,927,798 A | 5/1990 | Baldi | |
| 5,077,257 A | 12/1991 | Baldi | |
| 5,470,748 A * | 11/1995 | Hayden | G01N 25/4846 422/51 |
| 5,711,146 A | 1/1998 | Armstrong et al. | |
| H1948 H | 3/2001 | Rusek et al. | |
| 6,824,555 B1 * | 11/2004 | Towler | A61B 18/06 128/898 |
| 6,893,436 B2 | 5/2005 | Woodard et al. | |
| 6,960,203 B2 | 11/2005 | Xiao et al. | |
| 7,309,336 B2 | 12/2007 | Ashley et al. | |
| 8,343,095 B2 | 1/2013 | Cressman | |

(Continued)

OTHER PUBLICATIONS

Y Voloshin, J Manganaro, A Lawal. Kinetics and Mechanism of Decomposition of Hydrogen Peroxide over Pd/SiO2 Catalyst. Oct. 8, 2008, Ind. Eng. Chem. Res., 47, 8119-8125.*

(Continued)

*Primary Examiner* — Ronald Hupczey, Jr.
*Assistant Examiner* — Bo Ouyang
(74) *Attorney, Agent, or Firm* — Brinks Gilson & Lione

(57) ABSTRACT

The invention relates to devices, systems, and methods for heating tissue, including ablating a tumor, using the catalyzed heat of decomposition of hydrogen peroxide solutions. A hydrogen peroxide solution is contacted with a catalyst to decompose the hydrogen peroxide and heat the distal tip of a catheter to a temperature effective to ablate a target tissue.

19 Claims, 1 Drawing Sheet

(56) References Cited

U.S. PATENT DOCUMENTS

| | | | |
|---|---|---|---|
| 2011/0152852 A1* | 6/2011 | Cressman | A61B 18/06 606/27 |
| 2012/0059286 A1* | 3/2012 | Hastings | A61N 7/022 601/2 |
| 2012/0215212 A1 | 8/2012 | Selzer et al. | |
| 2012/0253192 A1 | 10/2012 | Cressman | |

OTHER PUBLICATIONS

CJ Marzzacco. The Enthalpy of Decomposition of Hydrogen Peroxide. Nov. 1, 1999, Journal of Chemical Education, vol. 76 No. 11.*

* cited by examiner

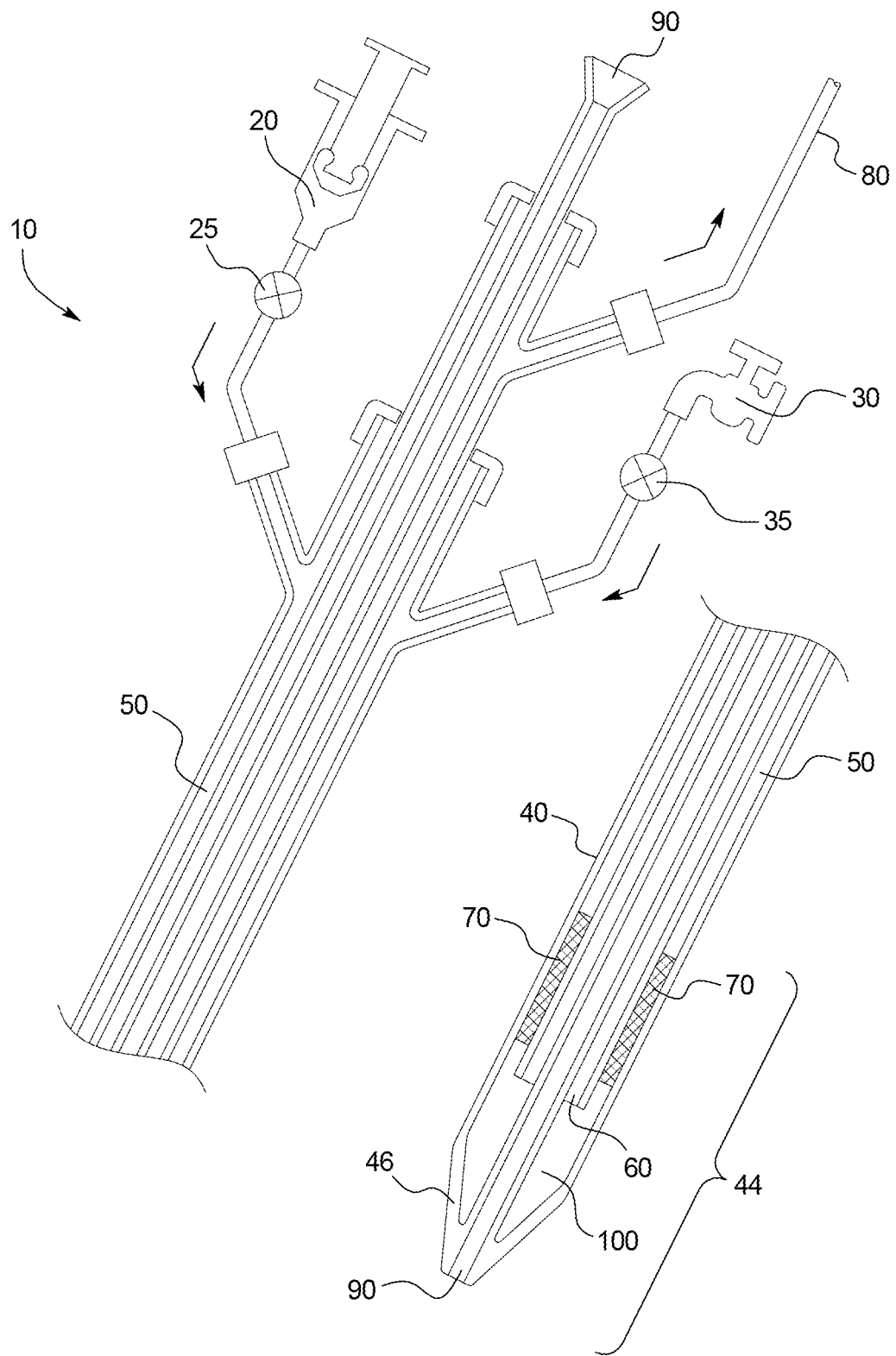

CATALYZED EXOTHERMIC ABLATION DEVICE

RELATED APPLICATIONS

The present patent document claims the benefit of the filing date under 35 U.S.C. §119(e) of Provisional U.S. Patent Application Ser. No. 61/777,051, filed Mar. 12, 2013, which is hereby incorporated by reference.

TECHNICAL FIELD

The present invention relates to devices, systems, and methods for ablating tissue (e.g., a tumor) by heating a target tissue with the energy produced from the catalytic decomposition of hydrogen peroxide solutions.

BACKGROUND OF THE INVENTION

One approach to removing an undesired source of tissue growth involves the application of sufficient thermal energy to the target growth to remove the tissue by ablation. Various types of growths that can be removed through thermal ablation include tumors, warts, etc. In the ablation technique, the tissue is eliminated by necrosis, and allowed to slough away. Compared with surgical removal of tissue, ablation therapy may have reduced morbidity, lower cost, and may spare surrounding tissue. Ablation has been used to remove a variety of tumor types such as in liver, lung, breast, pancreas, bile duct, bone, and kidney.

Existing ablation techniques include the use of RF energy. RF ablation techniques, however, suffer from the disadvantage that special precautions are needed to use an RF generator in conjunction with a magnetic resonance imager because of the risk from the displacement force of the magnet. Cryoablation has also been used to ablate tissue but is susceptible to a high rate of reoccurrence. Techniques have also been described for ablating tissue with the heat generated from a chemical reaction. Existing thermochemical ablation techniques, however, can suffer from the complications associated with handling of multiple potentially hazardous chemicals in liquid or gaseous form and the removal of the reaction by-products from the treatment site without contamination of the target tissue from the reactants or their by-products.

Thus, there exists a need for simple and low-cost techniques to conduct controlled ablation of tissue under a variety of circumstances.

SUMMARY OF THE INVENTION

The present invention relates to devices, systems, and methods for heating tissue (e.g., a tumor) by harnessing the energy from the catalyzed decomposition of hydrogen peroxide solutions. The invention relates in particular to systems and methods for tumor ablation.

One aspect of the invention provides a catalyzed exothermic ablation system comprising a source of hydrogen peroxide, a source of neutralizing solution, a catalyst, and a catheter. The catheter according to this aspect of the invention has a proximal end, a distal end, and an enclosed heat chamber located at the distal end of the catheter. The enclosed heat chamber is in fluid communication with the catalyst and the source of neutralizing solution. A heated solution in the enclosed heat chamber may transfer its energy through the distal tip of the catheter to heat and/or ablate a target tissue.

Another aspect of the invention provides a method of heating and/or ablating tissue by using the heat generated from the catalyzed decomposition of a solution of hydrogen peroxide. One embodiment provides a method of heating tissue by advancing a catheter comprising a catalyst and a distal tip into an operative position within a patient, contacting a solution of hydrogen peroxide with the catalyst to heat the distal tip of the catheter; and heating a tissue with the distal tip of the catheter.

BRIEF DESCRIPTION OF THE DRAWINGS

The embodiments will be further described in connection with the attached drawing figures. It is intended that the drawings included as a part of this specification be illustrative of the exemplary embodiments and should in no way be considered as a limitation on the scope of the invention. Indeed, the present disclosure specifically contemplates other embodiments not illustrated but intended to be included in the claims. Moreover, it is understood that the figures are not necessarily drawn to scale.

FIG. 1 illustrates an exemplary embodiment of the catalytic thermal ablation system.

DETAILED DESCRIPTION

The decomposition of hydrogen peroxide results in the formation of water and oxygen according to the following equation:

$$2H_2O_2 \rightarrow 2H_2O + O_2$$

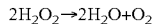

The decomposition of hydrogen peroxide as shown in the foregoing equation is an exothermic reaction with a $\Delta H = 23.4$ kcal/mole. Although the normal decomposition rate of hydrogen peroxide is slow, the presence of transition metals or alkali can accelerate its decomposition. The rate of decomposition also increases with increasing temperature as about a 2.3-fold increase in decomposition rate is observed with every 10° C. rise in temperature.

The amount of heat produced by the decomposition of aqueous solutions of $H_2O_2$ depends on the concentration of $H_2O_2$. The decomposition of higher concentrations of $H_2O_2$ produces greater amounts of heat and accordingly greater increases in temperature. For concentrations up to about 64% $H_2O_2$, it has been estimated from calculations that the maximum adiabatic decomposition temperature is about 100° C. At about 64% $H_2O_2$, enough water is present in the $H_2O_2$ solution to absorb the heat of decomposition by the production of steam. At higher concentrations of $H_2O_2$, there is no longer enough water to dissipate the heat of decomposition as steam, resulting in temperature increases above 100° C. and the thermal expansion of the gas produced by decomposition.

The decomposition of solutions with a concentration of $H_2O_2$ of about 10% can also raise the adiabatic solution temperature from ambient temperature to about 100° C. At concentrations between about 10% and about 60%, the maximum solution temperature from decomposition remains relatively constant at about 100° C., although the volumetric expansion of the resultant gas increases from about 45 to about 1500 times the volume of the $H_2O_2$ solution over the foregoing concentration range. The increase in solution temperature from the decomposition of solutions having less than 10% $H_2O_2$ may also produce a significant rise in solution temperature. The decomposition of a 5% solution, for example, may raise the solution temperature to between about 50° C. to about 100° C.

Referring to FIG. 1, one embodiment of a system 10 for catalyzed exothermic heating of tissue is shown. In the exemplary embodiment of FIG. 1, a source of hydrogen peroxide solution 20 is in fluid communication with a delivery channel 50 within the catheter 40. The catheter shaft may be the product of an extruded, rigid or flexible polymer. The extrusion possesses a multitude of lumens which may be adjacent or concentric. The delivery channel 50 represents such a lumen that runs along the longitudinal axis of the catheter and extends circumferentially along the interior wall of the catheter to form an annular space through which the hydrogen peroxide solution may flow from the proximal end of the catheter to the distal end. Concentric with the delivery channel 50 and disposed in a radially inward position is a pressure relief channel 60. The pressure relief channel 60 also runs along the longitudinal axis of the catheter in parallel with delivery channel. In the embodiment of FIG. 1, the pressure relief channel also forms an annular space due to the presence of a guidewire lumen 90, which passes through the center of the catheter. The pressure relief channel 60 provides a passage through which effluent may pass from the distal end 44 of the catheter out through the exit port 80. It is understood that the relative positioning of the delivery channel and pressure relief channel is not critical and that their positions may be reversed relative to the embodiment of FIG. 1. The pressure relief channel may have a greater cross-sectional area than the delivery channel to more effectively relieve pressure. Alternatively, the delivery and pressure-relief channels may be positioned adjacent to one another rather than concentric. Likewise, the guidewire lumen 90 is an optional feature that need not be present in the system.

Although the catheter, the delivery channel and the pressure-relief channel of embodiment of FIG. 1 are generally described as having a circular cross-sectional profile, the invention is not limited to this particular shape. The delivery and pressure-relief channels, for example, may have any shape that accommodates the transfer of fluid from the source of hydrogen peroxide solution toward the catalyst and enclosed heat chamber or accommodates the release of pressure out the pressure relief channel. Preferably, the pressure relief channel has a round cross-section to ensure that it resists pressure-related deformation.

A catalyst 70 is located in the interior of the catheter at its distal end 44. An enclosed heat chamber 100 is also located at the distal end 44. In the embodiment of FIG. 1, catalyst 70 is located inside the distal end of the delivery channel 50. However, the location of the catalyst is not limited to this precise location. For example, the catalyst may be positioned in a more proximal or a more distal location. For instance the catalyst may be located in the enclosed heat chamber 100 or straddling the enclosed heat chamber and the distal end of the deliver channel.

A variety of transition metals may be used in the catalyst 70 to promote the decomposition of $H_2O_2$. Suitable metals include elements from Groups VB, VIB, VIIB, VIII, and IB of the Periodic Table of Elements such as, for example, vanadium, chromium, manganese, iron, cobalt, nickel, copper, niobium, molybdenum, technetium, ruthenium, rhodium, palladium, silver, tantalum, wolfram, rhenium, osmium, iridium, platinum, and gold, or mixtures thereof. One particular combination of transition metals comprises a mixture of ruthenium plus iridium and/or platinum as described in U.S. Pat. No. 5,711,146, which is incorporated herein by reference in its entirety. The catalyst may also include a transition metal cation or transition metal oxide chosen from the foregoing transition metals. Alloys may also be employed such as, but not limited to, brass. Alternatively, the catalyst for decomposition of $H_2O_2$ solutions may include a carbonaceous char such as those described in U.S. Pat. No. 5,470,748, which is incorporated herein by reference in its entirety. The catalyst 70 may also include an alkaline promoter mixed with a transition metal salt as described in U.S. Statutory Invention Reg. No. H1948 H, which is herein incorporated by reference in its entirety. In one embodiment of the invention, the catalyst comprises platinum metal.

The catalyst 70 may also include a porous support material such as alumina, silica, aluminosilicate, diatomaceous earth, porous clays, titanium dioxide, calcium carbonate, barium sulfate, polar ceramics, or combinations thereof. Porous support materials are known in the art and described in U.S. Pat. No. 5,711,146 and U.S. Statutory Invention Reg. No. H1948 H. For example, a transition metal salt with or without an alkaline promoter may be deposited on or impregnated into the support material and activated by calcining.

The catalyst 70 may alternatively comprise a transition metal or mixture of transition metals in the form of a conventional wire screen as is generally known in the art. For example, a wire screen/mesh may be made by plating (e.g., electroplating) or depositing (e.g., vapor deposition) the desired transition metals onto wire mesh of a base metal(s) (e.g., nickel, copper). Alternatively, a wire mesh may be made of the desired transition metal by drawing wires from a bar of the metal or mixture of metals and weaving the wires into a mesh. In one embodiment of the invention, for example, the catalyst comprises a wire screen that includes platinum or mixtures of platinum with other metals.

In yet other alternative arrangements, the catalyst may take the form of a foil, ribbon, metal wool, sheets, perforated and/or fluted and/or dimpled foil or sheet, tubes, blocks, or a honeycomb structure as described in U.S. Pat. Nos. 4,292,208, 4,927,798, and 5,077,257, which are herein incorporated by reference in their entireties.

The distal end of the catheter in the embodiment of FIG. 1 includes a distal tip 46. The distal tip 46 is sealingly connected to the main body of the catheter and forms an enclosed space for the enclosed heat chamber. Thus, the distal tip contains the working fluids of the device. The distal tip is adapted to transfer heat from the enclosed heat chamber to a target tissue such as a tumor, in order to ablate the tumor. The distal tip may be made of any suitable material for transferring heat to the target tissue, such as, for example, a metal or metal alloy. Suitable materials include stainless steel, titanium, copper, nickel, gold, silver, aluminum, alloys, brass, bronze, or nitinol. The distal tip may have any of a number of different shapes. For example, the tip may be blunt, conical, trocar, beveled, rounded, bent, hook-shaped, angled, or other shape depending on the particular application. The device may have a cutting/burrowing feature at the distal tip.

In operation, a hydrogen peroxide solution is supplied via the delivery channel 50 to the catalyst 70. Upon contact with the catalyst, the hydrogen peroxide in the solution undergoes decomposition to water and oxygen, liberating heat in the process. The reaction by-products and the solvent from the hydrogen peroxide solution pass into the enclosed heat chamber where the reaction energy is transmitted through the distal tip to the target tissue.

A source of cooling or neutralizing solution 30 is also provided to allow an operator to moderate the temperature in the enclosed heat chamber, if necessary. For simplicity of description the cooling/neutralizing solution is referred to hereinafter as a "neutralizing solution." The term "neutralizing," however, is used in a broader sense than an adjustment of the pH of a solution to about 7. A "neutralizing solution" includes a solution that can dilute, cool, moderate, or quench a reaction, or alternatively flush the device to remove excess reactants or by-products.

Excess neutralizing solution, hydrogen peroxide solution, and reaction by-products may be removed from the enclosed heat chamber through the pressure-relief channel 60. Generally, the addition of hydrogen peroxide solution or neutralizing solution provides sufficient positive pressure to force fluid from the enclosed heat chamber back up through the pressure relief channel. As an alternative arrangement to the system, however, a source of suction may remove fluids from the enclosed heat chamber under reduced pressure.

Ablation of living tissue occurs with elevated temperature. Above 43° C., the time required to cause cell death is halved with each degree centigrade increase in temperature. At a temperature of about 46° C. for about 1 hour, irreversible damage occurs to living cells. Most mammalian cells do not survive at temperatures exceeding 49° C. for an extended period of time. At about 50-52° C., cell death occurs in about 4-6 minutes. At temperatures from about 60° C. to about 100° C., cell death is essentially instantaneous. At temperatures above 105° C., vaporization and charring of tissue occurs, thereby reducing the effectiveness of continued ablation therapy.

The hydrogen peroxide solution is supplied to the delivery channel and catalyst at an appropriate rate to supply energy to the distal tip sufficient to ablate or cauterize the targeted tissue according to the temperature parameters described herein. The incoming flow of hydrogen peroxide solution may be interrupted to lower the device temperature, or the neutralizing fluid may be introduced to moderate the rate of reaction and consequent heating of the distal tip. A control valve 25 may be used to control the rate of addition of hydrogen peroxide solution. Introduction of the neutralizing solution may be controlled using a valve 35. At the end of an ablation procedure, the hydrogen peroxide flow is discontinued and the surrounding fluids immediately carry heat away from the low-mass working surface. The flow may be reactivated as needed for completion of the procedure.

The amount of heating in ° C. will depend largely on the concentration of the $H_2O_2$ solution, the rate of addition, and the rate of dissipation of heat to the surroundings. The rate of addition and the concentration of the $H_2O_2$ solution may be varied as needed according to the particular application. According to a general method of the invention, the rate of addition and the concentration of $H_2O_2$ are adjusted to maintain a temperature at the distal tip of the catheter between about 46° C. to about 100° C. (i.e., a temperature sufficient to ablate a tumor). In another method, the distal tip is heated to about 46° C. to about 50° C. In another method, the distal tip is heated to about 50° C. to about 60° C. In another method, the distal tip is heated to about 60° C. to about 100° C. In another method, the distal tip is heated to about 60° C.

In one aspect of the invention, the concentration of the $H_2O_2$ solution to be used according to the invention is a concentration effective to heat the temperature of the distal tip sufficient to ablate a target tissue. For example, in one embodiment, the concentration of the $H_2O_2$ solution is effective to heat the temperature at the distal tip of the catheter to between about 46° C. to about 100° C. In another embodiment, the concentration of the $H_2O_2$ solution is effective to heat the distal tip to about 46° C. to about 50° C. In another embodiment, the concentration of the $H_2O_2$ solution is effective to heat the distal tip to about 50° C. to about 60° C. In another embodiment, the concentration of the $H_2O_2$ solution is effective to heat the distal tip to about 60° C. to about 100° C. In another embodiment, the concentration of the $H_2O_2$ solution is effective to heat the distal tip to about 60° C. Particular concentrations of the $H_2O_2$ solution to be used according to the invention may vary from about 5% up to about 60%. For example, suitable solution concentrations include, but are not limited to, about 5% to about 10%, about 5% to about 25%, about 10% to about 25%, about 10% to about 50%, and about 10% to about 60%.

The system 10 may also be equipped with a temperature sensor and the necessary circuitry to permit more accurate monitoring and control of the tissue heating process. MRI thermography may be used to monitor the temperature of the distal tip 46 and the surrounding tissue. The isotherm regions created by heating and ablation may be visualized with the imager to determine the extent of tissue ablation.

The ablation procedure may be performed with percutaneous, laparoscopic, or open-surgical approaches. The choice depends on the condition of the patient, tumor size, number, location, or growth pattern. The ablation device may be placed through the skin and into the tumor with imaging guidance. Percutaneous ablation may be monitored by real-time ultrasound imaging, computed tomography, or magnetic resonance imaging.

Once the device is introduced into a body cavity, it is positioned at an operative distance from a treatment site. An "operative position" or an "operative distance" refers to a positioning of the distal tip at a sufficient proximity to a tumor such that heat from the distal tip can ablate tumor tissue. An "operative position" thus encompasses positions wherein the distal tip may or may not be in physical contact with a tumor.

The invention may be used to ablate a range of tumor types such as, for example, lung tumors, hepatocellular carcinoma, bone tumors, breast tumors, pancreas tumors, bile duct tumors, renal and retroperitoneal tumors, osteoid osteomas, colorectal cancer, hepatic and cerebral metastases.

In one embodiment of a method of heating tissue according to the invention, a catheter comprising a catalyst and a distal tip is advanced into an operative position within a patient, a solution of hydrogen peroxide is contacted with the catalyst to heat the distal tip of the catheter, and heating the tissue with the distal tip of the catheter. In another embodiment, the hydrogen peroxide solution comprises a concentration of hydrogen peroxide having a heat of decomposition sufficient to heat the distal tip to a temperature effective to ablate tissue, the method also including the step of ablating the tissue. In another embodiment, the solution of hydrogen peroxide is contacted with the catalyst to heat the distal tip of the catheter to about 46° C. to about 100° C. In another embodiment of the foregoing method, the catalyst comprises platinum. In another embodiment, the catalyst comprises palladium. In yet another embodiment, the hydrogen peroxide solution has a % hydrogen peroxide between about 5% or 10% and about 25%.

The foregoing description of the invention has been presented for purposes of illustration and description, and is not intended to be exhaustive or to limit the invention to the precise form disclosed. The description was selected to best explain the principles of the invention and practical application of these principals to enable others skilled in the art to best utilize the invention in various embodiments and various modifications as are suited to the particular use contemplated.

What is claimed is:

1. A system for catalyzed exothermic heating of tissue comprising:
   a source of hydrogen peroxide solution;
   a source of neutralizing solution;
   a catalyst in fluid communication with the source of hydrogen peroxide; and
   a catheter, the catheter comprising a proximal end, a distal end, a distal tip, and an enclosed heat chamber located at the distal end of the catheter, the enclosed heat chamber being in fluid communication with the catalyst and the source of neutralizing solution;

the source of neutralizing solution being located external to the catheter.

2. The system of claim 1 wherein the catheter further comprises a delivery channel extending along the longitudinal axis of the catheter and having proximal and distal ends, the proximal end of the delivery channel being in fluid communication with the source of hydrogen peroxide solution and the distal end of the delivery channel being in fluid communication with the enclosed heat chamber.

3. The system of claim 2 wherein the catheter further comprises a pressure relief channel extending along the longitudinal axis of the catheter and having proximal and distal ends, the distal end of the pressure relief channel being in fluid communication with the enclosed heat chamber.

4. The system of claim 3 wherein the delivery channel and the pressure relief channel are arranged concentrically.

5. The system of claim 3 wherein:
the hydrogen peroxide solution comprises a concentration of hydrogen peroxide having a heat of decomposition sufficient to heat the distal tip to a temperature effective to ablate tissue;
the catalyst comprises one or more of a transition metal, a transition metal cation, a transition metal oxide, or an alloy, and is located at the distal end of the catheter; and
the distal tip is metallic.

6. The system of claim 5 wherein the heat of decomposition is sufficient to heat the distal tip to 46° C. to 100° C.

7. The system of claim 5 wherein the concentration of hydrogen peroxide is to 5% to 25%.

8. The system of claim 1 wherein the catheter further comprises a pressure relief channel extending along the longitudinal axis of the catheter and having proximal and distal ends, the distal end of the pressure relief channel being in fluid communication with the enclosed heat chamber.

9. The system of claim 1 wherein the hydrogen peroxide solution comprises a concentration of hydrogen peroxide having a heat of decomposition sufficient to heat the distal tip to a temperature effective to ablate tissue.

10. The system of claim 9 wherein the heat of decomposition is sufficient to heat the distal tip to 46° C. to 100° C.

11. The system of claim 9 wherein the concentration of hydrogen peroxide is 5% to 25%.

12. The system of claim 1 wherein the catalyst is located at the distal end of the catheter.

13. The system of claim 1 wherein the catheter further comprises a guidewire lumen extending longitudinally therethrough.

14. The system of claim 1 further comprising a temperature sensor.

15. The system of claim 1 wherein the distal tip is metallic.

16. The system of claim 1 wherein the catalyst comprises one or more of a transition metal, a transition metal cation, a transition metal oxide, or an alloy.

17. A method of heating tissue with a thermal tip catheter comprising the steps of:
advancing a catheter comprising a catalyst and a distal tip into an operative position within a patient;
contacting a solution of hydrogen peroxide with the catalyst to heat the distal tip of the catheter, the hydrogen peroxide solution comprising a concentration of hydrogen peroxide having a heat of decomposition sufficient to heat the distal tip to a temperature effective to ablate a tissue of the patient following contacting with the catalyst; and
heating the tissue of the patient with the distal tip of the catheter sufficient to ablate the tissue.

18. The method of claim 17 wherein the solution of hydrogen peroxide is contacted with the catalyst to heat the distal tip of the catheter to 46° C. to 100° C.

19. The method of claim 17 wherein the concentration of hydrogen peroxide is 5% to 25%.

* * * * *